United States Patent [19]

Rautenstrauch et al.

[11] Patent Number: 5,728,866
[45] Date of Patent: Mar. 17, 1998

[54] PROCESS FOR THE PREPARATION OF (+)-(1R)-CIS-3-OXO-2-PENTYL-1-CYCLOPENTANEACETIC ACID

[75] Inventors: Valentin Rautenstrauch, Bernex; Jean-Jacques Riedhauser, Certoux, both of Switzerland

[73] Assignee: Firmenich SA, Geneva, Switzerland

[21] Appl. No.: 591,509

[22] PCT Filed: Jun. 21, 1995

[86] PCT No.: PCT/IB95/00505

§ 371 Date: Feb. 7, 1996

§ 102(e) Date: Feb. 7, 1996

[87] PCT Pub. No.: WO96/00206

PCT Pub. Date: Jan. 4, 1996

[30] Foreign Application Priority Data

Jun. 23, 1994 [CH] Switzerland ............... 2006/94

[51] Int. Cl.$^6$ .............. C07C 69/74; C07C 61/06
[52] U.S. Cl. .............. 560/122; 560/115; 562/504
[58] Field of Search .............. 560/122, 115; 562/504

[56] References Cited

U.S. PATENT DOCUMENTS

| | | | |
|---|---|---|---|
| 3,158,644 | 11/1964 | Demole et al. | 560/122 |
| 3,754,016 | 8/1973 | Oberhansli | 560/122 |
| 3,954,834 | 5/1976 | Cohen | 560/122 |
| 3,978,108 | 8/1976 | Teisseire et al. | 560/122 |
| 4,014,919 | 3/1977 | Johnson et al. | 560/122 |
| 4,039,563 | 8/1977 | Tanaka et al. | 560/122 |
| 4,045,489 | 8/1977 | Wiegers et al. | 568/387 |
| 4,072,755 | 2/1978 | Buendia et al. | 560/122 |
| 4,237,308 | 12/1980 | Torii et al. | 560/122 |
| 4,280,934 | 7/1981 | Schulte-Elte | 560/122 |
| 4,294,863 | 10/1981 | Mookherjee et al. | 560/122 |
| 5,300,489 | 4/1994 | Boden et al. | 512/8 |
| 5,302,745 | 4/1994 | Winter | 560/126 |
| 5,372,994 | 12/1994 | Yamada et al. | 512/8 |
| 5,436,226 | 7/1995 | Lulai et al. | 504/291 |

FOREIGN PATENT DOCUMENTS 69-18228  6/1971  Netherlands.

OTHER PUBLICATIONS

B. Heiser et al., "New Efficient Methods for the Synthesis and In-Situ Preparation of Ruthenium(II) Complexes of Atropisomeric Diphosphines and Their Application in Asymmetric Catalytic Hydrogenations," *Tetrahedron: Asymmetry* vol. 2, No. 1, (1991) pp. 51–62.

E. Demole et al., "Isolement et determination de la structure du jasmonate de methyle, constituant odorant caracteristique de l'essence de jasmin," *Helvetica Chimica* ACTA (1962), pp. 675–685.

O. Miersch et al., "(+)-7-ISO-Jasmonic Acid and Related Compounds From Botryodiplodia Theobromae." *Phytochemistry*, vol. 26, No. 4 (1987) pp. 1037–1039.

K. Wan et al., "Asymmetric Hydrogenation in Water by a Rhodium Complex of Sulfonated 2,2'-Bis(diphenylphosphino)-1,1'-binaphthyl (binap)," *J. Chem. Soc.* (1993) pp. 1262–1264.

M.J. Burk, "$C_2$-Symmetric Bis(phospholanes) and Their Use in Highly Enantioselective Hydrogenation Reactions," *J. Am. Chem. Soc.*, vol. 113, No. 22 (Oct. 1991) pp. 8518–8519.

*Primary Examiner*—Deborah Lambkin
*Attorney, Agent, or Firm*—Pennie & Edmonds LLP

[57] ABSTRACT

A method for preparing 3-oxo-2-pentyl-1-cyclopentaneacetic acid or methyl 3-oxo-2-pentyl-1-cyclopentaneacetate, essentially in the form of the (+)-(1R)-cis isomer thereof. The method includes the steps of (a) catalytically hydrogenating a compound of the formula (I),

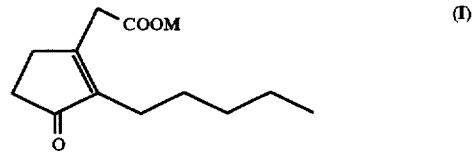

wherein M is a hydrogen atom, an alkali metal or alkaline earth metal atom, or a group $NR_4$, where R is a hydrogen or a lower alkyl radical, in a suitable solvent and in the presence of a catalyst consisting of an Ru(II) complex comprising chiral ligands that contain a 2,2'-bis (diphenylphosphino)-1,1'-dinaphthyl (BINAP) radical or a 1,2-bis(2,5-dialkylphospholano)benzyl (DuPHOS) radical, wherein the alkyl is a $C_2$ or $C_3$ radical, to give a compound of formula (II).

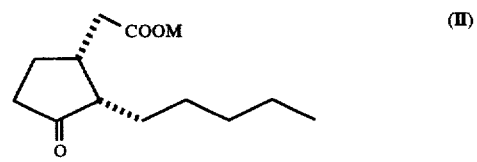

wherein M has the meaning given above, essentially in the form of the (+)-(1R)-cis isomer thereof;

(b) if required, acidifying, in a per se known manner, the compound of formula (II), wherein M is an alkali metal or alkaline earth metal atom, or a group $N_4$, where R is hydrogen or a lower alkyl radical, to give (+)-(1R)-cis-3-oxo-2-pentyl-1-cyclopentaneacetic acid; and (c) if required, esterifying the resulting (+)-(1R)-cis-3-oxo-2-pentyl-1-cyclopentaneacetic acid under suitable conditions to form methyl (+)-(1R)-cis-3-oxo-2-pentyl-1-cyclopentaneacetate.

18 Claims, No Drawings

PROCESS FOR THE PREPARATION OF (+)-(1R)-CIS-3-OXO-2-PENTYL-1-CYCLOPENTANEACETIC ACID

This application is a 371 of PCT/IB1995/00505 filed Jun. 21, 1995.

TECHNICAL FIELD AND PRIOR ART

The present invention relates to the field of organic synthesis and, more particularly, to that of the stereoselective and enantioselective synthesis of optically active compounds. It concerns in particular the preparation of (+)-(1R)-cis-3-oxo-2-pentyl-1-cyclopentaneacetic acid, or (+)-(1R, 2S)-3-oxo-2-pentyl-1-cyclopentaneacetic acid, in a pure optically active form, as well as its methyl ester.

The structure of (+)-(1R)-cis-3-oxo-2-pentyl-1-cyclopentaneacetic acid is known. It has in fact been described by O. Miersch et al. in Phytochem. 26, 1037 (1987). According to these authors, the above-mentioned acid was extracted from a culture of *Botryodiplodia theobromae* isolated from Cuban origin oranges. However, to our knowledge, there is no prior art description of any synthetic method for preparing this acid which is susceptible of convenient industrial application.

The present invention brings precisely a solution to this problem. It provides the above-mentioned acid with excellent optical purity and essentially in the form of its (+)-(1R)-cis configuration isomer. This is all the more important in that (+)-(1R)-cis-3-oxo-2-pentyl-1-cyclopentaneacetic acid is a useful product for the preparation of methyl (+)-(1R)-cis-3-oxo-2-pentyl-1-cyclopentaneacetate, the preferred isomer, from an olfactive point of view, of methyl dihydrojasmonate, also known under the tradename of Hedione® (origin: Firmenich SA, Geneva, Switzerland), a much appreciated ingredient of vast use in perfumery.

Amongst the four optically active isomers of methyl dihydrojasmonate or Hedione®, it is in fact known that methyl (+)-(1R)-cis-3-oxo-2-pentyl-1-cyclopentaneacetate possesses at best the sought-after Hedione® odor characters, and namely its jasmine note. Thus, obtaining optically pure methyl (+)-(1R)-cis-3-oxo-2-pentyl-1-cyclopentaneacetate is of capital importance in perfumery. If one considers, in addition, that to this day there is no synthesis of this compound that can be exploited on an industrial scale, the value of the present invention becomes quite understandable, since the latter renders it possible to industrially produce a starting product that can be converted on a large scale and in a profitable manner into methyl (+)-(1R)-cis-3-oxo-2-pentyl-1-cyclopentaneacetate.

DESCRIPTION OF THE INVENTION

An object of the invention is therefore a process for the preparation of 3-oxo-2-pentyl-1-cyclopentaneacetic acid, or of methyl 3-oxo-2-pentyl-1-cyclopentaneacetate, essentially in the form of their (+)-(1R)-cis configuration isomer, characterized in that it comprises the following steps:

a) the catalytic hydrogenation, in an appropriate solvent and in the presence of a catalyst composed of a Ru (II) complex comprising chiral ligands which contain a 2,2'-bis(diphenylphosphino)-1,1'-binaphthyl (BINAP) type ligand or a 1,2-bis(2,5-dialkylphospholano) benzenyl (DuPHOS) type ligand, wherein the alkyl is a $C_2$ or $C_3$ radical, of a compound of formula

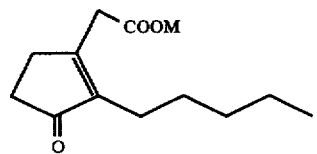

wherein M represents a hydrogen atom, an atom of an alkaline or alkaline-earth metal, or a $NR_4$ group, R representing hydrogen or a lower alkyl radical, to obtain a compound of formula

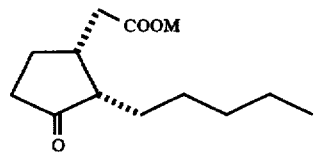

wherein M has the meaning indicated above, essentially in the form of an isomer of (+)-(1R)-cis configuration;

b) if necessary, the acidification, in a generally known manner, of the compound of formula (II) wherein M represents an atom of an alkaline or alkaline-earth metal or a $NR_4$ group, R representing hydrogen or a lower alkyl radical, to obtain (+)-(1R)-cis-3-oxo-2-pentyl-1-cyclopentaneacetic acid; and c) if necessary, the esterification, under appropriate conditions, of the (+)-(1R)-cis-3-oxo-2-pentyl-1-cyclopentaneacetic acid thus obtained to form methyl (+)-(1R)-cis-3-oxo-2-pentyl-1-cyclopentaneacetate.

By alkaline or alkaline-earth metal, it is understood here any one of the elements in group I, or respectively II, of Mendelejev's Periodic Table. In this context, there can be cited more particularly sodium, potassium, lithium, cesium, calcium and magnesium.

On the other hand, the lower alkyl radicals represented by symbol R, typically include linear or branched alkyl radicals, having 1 to 3 carbon atoms.

The catalysts used in the process of the invention are ruthenium (II) complexes in which this metal is bonded to chiral ligands of the BINAP type, i.e. derived from 2,2'-bis(diphenylphosphino)-1,1-binaphthalene, or of the family of 1,2-bis(phospholano)benzenes or DuPHOS. Concerning the latter, they contain, more particularly, radicals of the 1,2-bis(2,5-dialkylphospholano)benzenyl type, it being understood that "alkyl" means here a radical having 1 to 3 carbon atoms. Particular examples of commercially available products are 1,2-bis(2,5-dimethylphospholano)benzenyl, currently defined as Me-DuPHOS, and 1,2-bis(2,5-diethylphospholano)benzenyl or Et-DuPHOS (see, for example, M. J. Burk, J. Amer. Chem. Soc. 1991, 113,8518).

They are optically active compounds known for their high catalytic activity and which are currently used in the reactions of selective hydrogenation of olefines. However, in spite of the vast literature there-relative, namely in what concerns those containing BINAP type ligands, we were unable to find a single example of the use of such a catalyst in the hydrogenation of a cyclic and tetrasubstituted double bond, i.e. in which all the substituents are distinct from hydrogen, as is the case in the present process. It is with surprise that we observed that the above-mentioned hydrogenation provided a product having an essentially cis configuration, and this in excellent yield, even in the case where the starting product is 3-oxo-2-pentyl-1-cyclopentene-1-acetic acid and in spite of its instability.

The hydrogenation reaction which characterizes the process of the invention is the result of a large number of experiments carried out by means of a variety of catalysts, for instance rhodium based, the structure of which was furthermore sometimes very close to that of the Ru(II) catalysts presently used. The success of the latter is all the more surprising in that, in spite of the prior knowledge that said rhodium based catalysts favored the reduction of functions analogous to that of, in particular, the starting acid in the process of the invention, they turned out to be less efficient in the reduction of 3-oxo-2-pentyl-1-cyclopentene-1-acetic acid, unlike the ruthenium (II) catalysts used according to the invention.

Following a particular embodiment of the invention, the process is characterized in that 3-oxo-2-pentyl-1-cyclopentene-1-acetic acid is subjected to catalytic hydrogenation in an organic solvent, in the presence of bis (trifluoroacetato)[(+)-(R)-BINAP]ruthenium (II) or of bis (trifluoroacetato) [(−)-(R,R)-Et-DuPHOS]ruthenium (II).

As the organic solvent, there can be used any solvent of current use in this type of reactions, for example a chlorinated hydrocarbon, an alcohol or other. Improved yields were obtained when using a mixture of dichloromethane and methanol or of tetrahydrofuran and methanol.

Moreover, it was also observed that it was preferable to carry out the reaction in the presence of a nitrogen-containing organic base, for example a trialkylamine or a pyridine. The concentration in which this base can be added to the reaction medium varies within a molar ratio of 1:1 to 4:1, relative to the Ru (II) catalyst. Very good yields in final product were realized when triethylamine was added in a molar ratio comprised between 1.5:1 up to 4:1.

According to a particular embodiment of the process of the invention, the above-mentioned Ru (II) catalysts are prepared in situ, starting from commercial origin products and according to methods which are themselves known [see for example, B. Heiser et al., Tetrahedron: Asymmetry 1991, 2, pm. 43 and 51].

The starting 3-oxo-2-pentyl-1-cyclopentene-1-acetic acid is prepared by hydrolysis of methyl 3-oxo-2-pentyl-1-cyclopentene-1-acetate [described in U.S. Pat. No. 5,302, 745 or EP 583 564] under the conditions described further on.

The (+)-(1R)-cis-3-oxo-2-pentyl-1-cyclopentaneacetic acid thus obtained can then be used according to the invention to prepare methyl (+)-(1R)-cis-3-oxo-2-pentyl-1-cyclopentaneacetate, for example through treatment with an excess of diazomethane in ether solution.

Clearly, whenever the hydrogenation takes place in the presence of bis(trifluoroacetato)[(−)-(S)-2,2'-bis-(diphenylphosphino)-1,1'-binaphthyl] ruthenium (II) or of bis(trifluoroacetato)[(+)-(S,S)-Et-DuPHOS]ruthenium (II), there is obtained (−)-(1S)-cis-3-oxo-2-pentyl-1-cyclopentaneacetic acid, which can be used to prepare methyl (−)-(1S)-cis-3-oxo-2-pentyl-1-cyclopentaneacetate.

Another preferred embodiment of the invention is a process characterized in that a compound of formula (I) wherein M represents an atom of an alkaline or alkaline-earth metal, or a $NR_4$ group, R representing hydrogen or a lower alkyl radical, is subjected to catalytic hydrogenation, in an appropriate solvent and in the presence of a catalyst composed of a ruthenium (II) complex and(+)-(R)-BINAP-sulfonated.

The catalyst mentioned here-above is a ruthenium (II) complex with sulfonated (+)-(R)-2,2'-bis-(diphenylphosphino)-1,1'-binaphthyl, this chiral ligand being obtained by sulfonation of BINAP, in a manner analogous to that described by Kam-to Wan et al., J. Chem. Soc. Chem. Comm. 1993, 1262. According to these authors, the product of said sulfonation seems to be mainly a tetrasulfonated BINAP, i.e. $BINAP(SO_3Na_4)$, the sulfonate groups being apparently attached to the phenyl substituents of BINAP. The detailed conditions of the preparation of this type of catalyst are described further on.

Amongst the formula (I) compounds above-mentioned, used as starting products in this preferred embodiment of the invention, lithium 3-oxo-2-pentyl-1-cyclopentene-1-acetate will be preferably used.

Furthermore, these compounds of formula (I) wherein M represents an atom of an alkaline or alkaline-earth metal, or a $NR_4$ group, R representing hydrogen or a lower alkyl radical, are novel compounds which are also an object of the invention. They are prepared from 3-oxo-2-pentyl-1-cyclopentaneacetic acid as is described further on.

As the solvent, there will be preferably used a solvant which makes it possible to obtain a homogeneous reaction medium. To this end, an aqueous solvent can be used, namely water or a mixture of water with an alcohol, such as for example methanol. The relative proportions of water and the alcohol in these mixtures were not critical.

This embodiment of the process of the invention turned out to be very advantageous, allowing an easier and more efficient recovery of the catalyst, as well as of the hydrogenation product.

Furthermore, if desired, the process which is the object of the present invention can comprise additional steps which make it possible to further purify the products obtained as has been described up to here and namely improve the cis/trans isomeric ratio of these products in the cases where this could prove useful. Therefore, the invention also provides a process such as previously described, characterized in that it further comprises the purification of the obtained (+)-(1R)-cis-3-oxo-2-pentyl-1-cyclopentaneacetic acid or methyl (+)-(1R)-cis-3-oxo-2-pentyl-1-cyclo-pentaneacetate, which purification comprises:

a) the reduction of methyl (+)-(1R)-cis-3-oxo-2-pentyl-1-cyclopentane-acetate by means of lithium tri-(sec-butyl)-borohydride;

b) the treatment of the thus obtained reaction mixture with $H_2O_2$ and an excess of NaOH, followed by the acidification of the resulting salt, to obtain a mixture which contains essentially (+)-(1R,2S,3R)-3-hydroxy-2-pentyl-1-cyclopentaneacetic acid and (−)-(1R,2S,3S)-3-hydroxy-2-pentyl-1-cyclopentaneacetic acid;

c) the thermal treatment of said mixture in toluene, with water separation via azeotropic distillation, followed by a treatment with potassium carbonate to isolate the formed (−)-(1R,8S)-8-pentyl-2-oxabicyclo [3.2.1] octan-3-one; and d) the treatment of this lactone with NaOH, followed by acidification, to obtain practically pure (+)-(1R,2S,3R)-3-hydroxy-2-pentyl-1-cyclopentane-acetic acid;

e) the oxidation of this acid by means of pyridinium chlorochromate, in the presence of sodium acetate; and, if necessary, f) the esterification, under appropriate conditions, of the thus formed (+)-(1R)-cis-3-oxo-2-pentyl-1-cyclopentaneacetic acid, to obtain practically pure methyl (+)-(1R)-cis-3-oxo-2-pentyl-1-cyclopentaneacetate.

The above-mentioned purification method is based on the discovery that, unlike the classical processes for the reduction of compounds such as methyl 3-oxo-2-pentyl-1-cyclopentaneacetate and analogues, which processes resort to the use of, for example, sodium borohydride and lead to the formation of mixtures of all the isomers of 3-hydroxy-2-pentyl-1-cyclopentaneacetic acid [see for example, E. Demole et al., Helv. Chim. Acta 45, 675 (1962)], the use according to the invention of lithium tri-(sec-butyl)-borohydride or L-Selectride® (Aldrich), to reduce methyl (+)-(1R)-cis-3-oxo-2-pentyl-1-cyclopentane-acetate containing small amounts of trans isomers, turns out to be totally selective, providing only the compounds whose configuration is represented hereinafter (for racemic species)

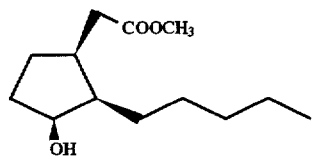

(±)-cis

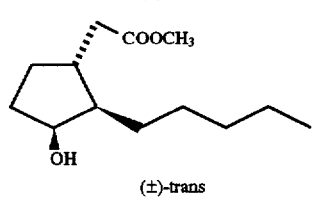

(±)-trans

This unexpected result proved to be of capital importance. In fact, it was established that, upon the saponification of these esters by means of NaOH, and the subsequent acidification of the resulting salts, which generates the formation of the corresponding acids, only the strictly cis-configuration acid having the formula

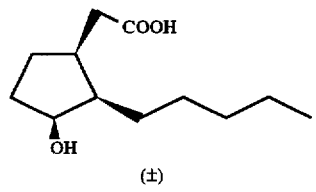

(±)

is able to form a lactone when subjected to thermal treatment in toluene, with azeotropic stripping of the water, such that the acid corresponding to the ester of formula (VI) remains inert under these conditions and can thus be separated from said formed lactone by means of potassium carbonate. This lactone, i.e. 8-pentyl-2-oxabicyclo[3.2.1]octan-3-one, or, as the case may be, one of its optically active isomers, can then be converted into acid (Va) by way of conventional methods. This entirely cis-configuration acid then makes it possible to obtain cis-3-oxo-2-pentyl-1-cyclopentaneacetic acid or, as the case may be, one of its enantiomers, in a pure form, by straight oxidation with pyridinium chlorochromate (PCC).

The process of the invention above-described thus makes it possible to eliminate the trans configuration isomers that may eventually be present in any one of the products obtained as described previously, i.e. by hydrogenation of compounds (I), eventually followed by the acidification of compounds (II) and the esterification of the formed 3-oxo-2-pentyl-1-cyclopentaneacetic acid having an essentially (1R)-cis configuration. This complementary purification method reveals itself particularly useful whenever the desired products previously obtained have a content in cis configuration isomers which is inferior to 95%.

According to a preferred embodiment of the invention, the pratically pure (+)-(1R,2S,3R)-3-hydroxy-2-pentyl-1-cyclopentaneacetic acid obtained in step d) of the process above is treated, before its oxidation, with an amine of formula

wherein R represents a phenyl or 1-naphthyl radical, the resulting salt being then crystallized in an appropriate organic solvent and the thus obtained crystalline salt subsequently acidified.

This preferred embodiment is most advantageous when it is desired to also eliminate all traces of (−)-(1S)-cis-3-oxo-2-pentyl-1-cyclopentaneacetic acid eventually present in the product of hydrogenation of compounds (I).

One can thus obtain (+)-(1R,2S,3R)-3-hydroxy-2-pentyl-1-cyclopentaneacetic acid with a purity of at least 95%, the oxidation of which will enable the formation, with similar purity, of the desired acid mentioned earlier.

It is clear from the above that the purification method according to the invention described hereabove is of far more general application than just the purification of the mentioned hydrogenation product. It is in fact an alternative process for preparing (+)-(1R)-cis-3-oxo-2-pentyl-1-cyclopentaneacetic acid, or its methyl ester, in a pure form, starting from racemic or optically active Hedione® in the form of any cis/trans isomer mixture whatsoever. Thanks to the essential and original steps of this process, to whit, the selective reduction of the starting Hedione® by means of L-Selectride® and the separation of the enantiomers of the c-3-hydroxy-c-2-pentyl-r-1-cyclopentaneacetic acid by means of the above-mentioned amines and their enantiomers, one can in this way prepare the desired (+)-(1R)-cis-3-oxo-2-pentyl-1-cyclopentaneacetic acid with a purity of at least 95%. The latter can then be converted, as is described above, into pure methyl (+)-(1R)-cis-3-oxo-2-pentyl-1-cyclopentaneacetate, or (+)-cis-Hedione®, the preferred isomer of this perfuming ingredient.

According to a variant of the invention, there is thus provided a process for the preparation of (+)-(1R)-cis-3-oxo-2-pentyl-1-cyclopentane-acetic acid or of methyl (+)-(1R)-cis-3-oxo-2-pentyl-1-cyclopentaneacetate, having a purity of at least 95%, characterized in that (+)-(1R,2S,3R)-3-hydroxy-2-pentyl-1-cyclopentaneacetic acid is oxidized by means of pyridinium chlorochromate, in the presence of sodium acetate, and, if applicable, the thus formed (+)-(1R)-cis-3-oxo-2-pentyl-1-cyclopentaneacetic acid is esterified under appropriate conditions.

The (+)-(1R,2S,3R)-3-hydroxy-2-pentyl-1-cyclopentaneacetic acid, used as starting product according to this variant of the process of the invention, is prepared via treatment of c-3-hydroxy-c-2-pentyl-r-1-cyclopentaneacetic acid with an amine of formula (V) such as defined above, followed by crystallization of the resulting salt in an appropriate organic solvent and the acidification of the crystallin salt thus obtained.

c-3-Hydroxy-c-2-pentyl-r-1-cyclopentaneacetic acid is in turn prepared in a pure state according to a method consisting in:

a) reducing methyl 3-oxo-2-pentyl-1-cyclopentaneacetate by means of lithium tri-(sec-butyl)-borohydride;

b) treating the reaction product with $H_2O_2$ and an excess of NaOH, followed by acidification, to obtain a mixture of c-3-hydroxy-c-2-pentyl-r-1-cyclopentaneacetic and t-3-hydroxy-t-2-pentyl-r-1-cyclopentaneacetic acids;

c) thermally treating said mixture in toluene, with water separation by azeotropic distillation, followed by a treatment with potassium carbonate, to isolate the formed (1RS,8SR)-8-pentyl-2-oxabicyclo [3.2.1] octan-3-one; and d) treating this lactone with NaOH, followed by acidification.

As previously cited, esterification of the practically pure (+)-(1R)-cis-3-oxo-2-pentyl-1-cyclopentaneacetic acid obtained according to this variant can be carried out by means of diazomethane, to provide methyl (+)-(1R)-cis-3-oxo-2-pentyl-1-cyclopentaneacetate, or (+)-cis-Hedione®, with equivalent purity.

Other esterification methods can also be used, as long as they retain the stereochemistry of the above-mentioned acid. According to a preferred embodiment, there is used dimethyl dicarbonate in methanol. According to another advantageous embodiment, there is used dimethyl sulfate and potassium carbonate in an appropriate solvent, for example acetone.

It is to be noted that (+)-(1R,2S,3R)-3-hydroxy-2-pentyl-1-cyclopentaneacetic acid, used as starting product in this variant of the process of the invention, can also be directly methylated, for example by reacting it with an excess of diazomethane in ether solution, to provide pratically pure methyl (+)-(1R,2S,3R)-3-hydroxy-2-pentyl-1-cyclopentaneacetate, which can then be converted into (+)-cis-Hedione® via oxidation.

If desired, the trans configuration optically active isomers of Hedione® can of course also be obtained in a pure form through epimerization of their (+)-(1R)-cis and (−)-(1S)-cis diastereomers prepared as mentioned above.

The processes above-described thus enable the preparation of (+)-(1R)-cis-3-oxo-2-pentyl-1-cyclopentaneacetic acid and of methyl (+)-(1R)-cis-3-oxo-2-pentyl-1-cyclopentaneacetate, the preferred isomer of Hedione®, with an optical purity of at least 95% and a strictly cis configuration. And this, thanks to conversions which can be practiced on an industrial scale. These products, having such stereochemical and optical purity, are novel compounds which are also the object of the invention.

The processes above further provide optically pure intermediate products which can be obtained on an industrial scale and are novel compounds. The invention also relates to these intermediate products, the use of which according to the invention enables the preparation of the above-cited optically pure final products.

The invention will now be described in further detail by way of the following examples, wherein the temperatures are indicated in degrees centigrade and the abreviations have the usual meaning in the art.

EMBODIMENTS OF THE INVENTION

EXAMPLE 1

Preparation of (+)-(1R)-cis-3-oxo-2-pentyl-1-cyclopentaneacetic acid a) (1RS,8SR)-8-pentyl-2-oxabicyclo[3.2.1]octan-3-one A 2 l three-neck double walled flask, equipped with a thermostat, a magnetic stirrer and an introduction funnel, kept under argon, was charged with a tetrahydrofuran (THF; 1M; 200 ml) solution of L-Selectride® introduced into the flask via cannula. The mixture was stirred, the temperature kept at −20° and a solution of Hedione® (methyl 3-oxo-2-pentyl-1-cyclopentaneacetate; 40 g; 177 mmole; cis/trans mixture 67:33) in 82 ml of THF was introduced dropwise during ca. 35 min. The mixture was stirred for 2 h at −20° and the temperature increased to 0°. Aqueous NaOH (3N; 250 ml) was added dropwise. After stopping the Ar flow, $H_2O_2$ (30%; 250 ml; Fluka) was introduced dropwise. After overnight heating at 65° and stirring, the product was allowed to cool and the THF stripped under reduced pressure.

The resulting aqueous alcaline solution was extracted 2× with ether. The aq. alcaline phase was acidified with 3N HCl, extracted 2× with ether, dried over $MgSO_4$ and concentrated. The product was retaken in 100 ml of toluene and heated to reflux with a water separator for 18 h to cyclize into lactone. After concentrating, there were obtained 29.1 g of a raw mixture containing the desired lactone.

This mixture was taken in ether and extracted 2× avec 100 ml of 1M aq. $K_2CO_3$. The aqueous phases were extracted 3× with ether and the ether extracts washed to neutrality with water. After drying over $MgSO_4$ and concentrating, 14.1 g of raw lactone were obtained. After bulb-to-bulb distillation under 13 Pa at 170°, 11.3 g of (1RS,8SR)-8-pentyl-2-oxabicyclo[3.2.1]octan-3-one (purity: 97%; 58 mmole; yield 48%) were obtained.

NMR($^1$H,360 MHz): 0.89(t, J=7, 3H); 1.20–1.63(8H); 1.63–1.78(2H); 1.87–2.03(2H); 2.06–2.18($^1$H); 2.36(d, J=20, 1H, covered by broad s, 2.32, 1H); 2.74(dxdxd, J=20, 2.0, 1.6, 1H); 4.61(broad s, 1H) δ ppm NMR($^{13}$C): 14.0(q); 22.6(t); 25.4(t); 28.0(t); 30.0(t); 31.9(t); 32.2(t); 34.5(d); 36.2(d); 44.8(d); 82.4(d); 171.1(s) δ ppm MS: 196(2,M+), 98(50), 84(95), 83(100), 82(81), 81(75), 67(50), 55(59)

Odor: lactonic, mushroom, fruity, floral

All the aqueous phases resulting from the operation above were combined and acidified with HCl 1N, extracted 3 times with ether, dried over $MgSO_4$ and concentrated under reduced pressure to provide 12.4 g of raw t-3-hydroxy-t-2-pentyl-r-1-cyclopentaneacetic acid.

b) c-3-hydroxy-c-2-pentyl-r-1-cyclopentaneacetic acid

A flask was charged with 16.08 g (82.0 mmole) of the lactone obtained under a), 33 ml of an aqueous solution of NaOH (99 mmole) and 57 ml of THF. It was stirred and heated to 70° during 4.5 h. Most of the THF was stripped by distillation. The mixture was cooled and extracted 2 times with ether, the extracts having been eliminated. The aqueous phase was acidified with aq. 3N HCl. After extracting 2 times with ether, the combined extracts were washed with water, dried over $MgSO_4$, filtered and concentrated. The thus obtained raw residue (16.2 g; yield 82%) formed crystals (m.p. 74°–76°). The desired acid thus obtained can be used as such in the following step or recrystallized in cyclohexane/ethyl acetate to provide a product having m.p. 79°–81° (colorless crystals). NMR($^1$H,360 MHz): 0.89(t, J=6, 3H); 1.22–1.53(8H); 1.57–1.95(5H); 2.32–2.53(3H); 4.22(t, J=3.5, 1H); ca 5.9–7.0(broad, 2 OH) δ ppm NMR ($^{13}$C): 14.1(q); 22.6(t); 25.1(t); 28.3(t); 29.5(t); 32.3(t); 33.6(t); 36.3(d); 36.5(t); 47.9(d); 74.8(d); 179.9(s) δ ppm MS: 84(82), 83(98), 82(70), 81(71), 79(56), 77(63), 55(94), 41(100)

c) (+)-(1R,2S,3R)-3-hydroxy-2-pentyl-1-cyclopentaneacetic acid and (−)-(1S,2R,3S)-3-hydroxy-2-pentyl-1-cyclopentaneacetic acid The crystalline acid obtained under b) (8.63 g; 40.3 mmole) was dissolved in ethanol (190 ml) and (+)-(R)-1-phenylethylamine [4.88 g; 40.3 mmole; Fluka purum, enantiomeric ratio (e.r.) 98:2]. The product was concentrated under reduced pressure and the residue was dissolved in 300 ml of a hot mixture of cyclohexane/ethyl acetate 5:1 (v/v), which was allowed to crystallize overnight. After filtration and air drying, 5.93 g of crystalline product having m.p. 127°–130°. This product was recrystallized in 250 ml of a mixture of solvents identical to that above-mentioned to provide 4.78 g of (1S,2R,3S)-3-hydroxy-2-pentyl-1-cyclopentaneacetate of (R)-1-phenylethylammonium [m.p. 132°–135°; $[\alpha]_{20}^{D}=-4°$ (c=1.10 g/100 ml, ethanol)]. This salt was taken in ether and extracted once with 35 ml of NaOH 1N. The ether phase was washed 2× with water and the combined aqueous phases extracted with ether. Drying of the combined organic phases over $MgSO_4$, filtration and concentration provide (+)-(R)-1-phenylethylamine which can be recycled.

The combined aqueous phases were acidified with 40 ml of aq. HCl (1N) and extracted 2× with ether. The product was dried over $MgSO_4$, filtered and concentrated to give 2.80 g of (−)-(1S,2R,3S)-3-hydroxy-2-pentyl-1-cyclopentaneacetic acid, in the form of a colorless oil (13.1 mmole; yield 92%).

This acid presented the analytical characters of the racemic acid described under b) and a $[\alpha]_{20}^{D}=-12°$ (c=1.15, ethanol) (purity: 99%; e.r. 99.2:0.8). Proceeding in a manner analogous to that described here-above, but using (−)-(S)-1-penylethylamine (Fluka purum; e.r. 98:2), there was obtained (1R,2S,3R)-3-hydroxy-2-pentyl-1-cyclopentaneacetate of (S)-1-phenyl-ethylammonium (m.p. 131°–132°; $[\alpha]_{20}^{D}=+4°$; c=1.05, ethanol) and (+)-(1R,2S,3R)-3-hydroxy-2-pentyl-1-cyclopentaneacetic acid having $[\alpha]_{20}^{D}=+11°$ (c=1.10, ethanol) (purity: 99%; e.r. 96.5:3.5).

These experiments were repeated with (+)-(R)-1-(1-naphthyl)ethylamine (Fluka purum; e.r.>99:1), which provided (1S,2R,3S)-3-hydroxy-2-pentyl-1-cyclopentaneacetate of (R)-1-(1-naphthyl)ethylammonium [m.p. 134°–136°; $[\alpha]_{20}^{D}=+4°$ (c=1.145, ethanol)], leading to (−)-(1S,2R,3S)-3-hydroxy-2-pentyl-1-cyclopentaneacetic acid. The absolute configuration of this acid was confirmed by X-rays of the intermediate salt.

On the other hand, (−)-(S)-1-(1-naphthyl)ethylamine (Fluka purum; e.r.>99:1) gave (1R,2S,3R)-3-hydroxy-2-pentyl-1-cyclopentaneacetate of (S)-1-(1-naphthyl)ethylammonium [m.p. 134°–135° $[\alpha]_{20}^{D}=-4°$(c=1.05, ethanol)] and (+)-(1R,2S,3R)-3-hydroxy-2-pentyl-1-cyclopentaneacetic acid.

d) (+)-(1R)-cis-3-oxo-2-pentyl-1-cyclopentaneacetic acid and (−)-(1S)-cis-3-oxo-2-pentyl-1-cyclopentaneacetic acid These acids were prepared from the hydroxyacids described under c), as follows.

A flask equipped with a thermometer and a cooling mantle, was charged with 5.66 g of PCC (26.3 mmole), 322 mg of anhydrous sodium acetate (3.93 mmole) and 30 ml of $CH_2Cl_2$. The suspension was cooled to −10°, stirred and the hydroxyacid (~13 mmole) in 10 ml of $CH_2Cl_2$ was added all at once. The mixture was stirred at −10° during 20 h. The reaction mixture was passed through a column of $SiO_2$ in ether, and likewise the solution of $CH_2Cl_2$ and the solutions from the washing of the reaction flask (with ether). The eluted solutions were concentrated to yield (+)-(1R)-cis-3-oxo-2-pentyl-1-cyclopentaneacetic acid having a purity of 95% and an enantiomeric ratio of 99:1.

The analytical characters of this compound were the following:

$[\alpha]_{20}^{D}=+71°$ (c=0.985, ethanol)
NMR(1H,360 MHz): 0.88(t, J=7, 3H); 1.17–1.47(7H); 1.55–1.69(1H); 1.80–1.95(1H); 1.98–2.22(1H); 2.13(dxd, J=15, 10, 1H); 2.20–2.37(3H); 2.46 (dxd, J=15, 5, 1H); 2.84(broad septet, J=5, 1H) δ ppm NMR($^{13}C$): 14.0(q); 22.5(t); 24.6(t); 25.6(t); 27.1(t); 31.8(t); 33.7(t); 35.1(t); 35.5(d); 52.6(d); 178.6(s); 219.5(s) δ ppm MS: 212(2,M+), 153(20), 142(31), 84(7), 83(100), 82(21), 67(6), 88(8)

Its (−)-(1S)configuration enantiomer was also obtained.

EXAMPLE 2

Preparation of (+)-(1R)-cis-3-oxo-2-pentyl-1-cyclopentaneacetic acid

Into a Schlenk type vessel, kept anhydrous and under Ar, there was injected the precatalytic solution (6.75 ml) containing 47 mg (0.05 mmole) of bis(trifluoro-acetato)[(+)-(R)-2,2'-bis-(diphenylphosphino)-1,1'-binaphthyl]ruthenium (II), 3-oxo-2-pentyl-1-cyclopentene-1-acetic acid (0.5 g, 2.4 mmole), $CH_2Cl_2$ (5 ml), methanol (5 ml) and triethylamine (10.28 mg, 0.1 mmole, 14 µl, dist. over KOH). After stirring for 5 min, the orange soltion was filtered through a single use filter (Acrodisc 0.45 µm) in a dry autoclave (100 ml/$10^7$ Pa) under Ar. The autoclave was then connected to a source of hydrogen and rinsed 5× with hydrogen at a pressure of $10^6$ Pa. The autoclave was then pressurized at $9×10^6$ Pa. Stirring at this pressure and 25° was carried out during 120 h. Afterwards, the pressure was gently released, the autoclave opened and the orange solution concentrated.

Analysis of the thus obtained (+)-(1R)-cis-3-oxo-2-pentyl-1-cyclopentaneacetic acid was carried out via the methyl (+)-(1R)-cis-3-oxo-2-pentyl-1-cyclopentaneacetate obtained upon adding diazomethane in ether solution. After the usual treatment, analysis by gas-liquid chromatography on chiral column (commercial origin alkylated cyclodextrine) of the ester thus obtained showed that it consisted of a mixture having 85% by weight of cis configuration isomers, of which 85% of (+)-(1R) and 15% of (−)-(1S) (enantiomeric excess e.e. 70%), and 15% of impurities, amongst which 5% of trans configuration isomers of said acid. Identical experiments, but using triethylamine in molar ratios comprised between 1.4:1 and 4:1, relative to the catalyst, provided the final product with equivalent optical purity.

The catalyst used was prior prepared in situ, according to the method described by B. Heiser, ref. cited, in this manner.

Ru(COD)($\eta^3$-methallyl)$_2$ (origin: Intex Chemikalien, Muttenz, Switzerland; 16 mg, 0.05 mmole) was mixed under Ar and in anhydrous conditions with trifluoroacetic acid (11.4 mg, 0.1 mmole) and methanol (0.25 ml). To the resulting suspension, there was added a solution of (+)-(R)-2,2'-bis(diphenylphosphino)-1,1'-binaphthalene (R-BINAP; origin: Fluka; 31 mg, 0.05 mmole) in a mixture of methanol (3 ml) and dichloromethane (3.5 ml) and the mixture was allowed to react under stirring at room temperature during 3 days. The pale yellow solution containing the catalyst (7.4 mmole/l) was used as such in the hydrogenation.

The 3-oxo-2-pentyl-1-cyclopentene-1-acetic acid used as starting product in this hydrogenation was prepared as follows, by saponification of methyl 3-oxo-2-pentyl-1-cyclopentene-1-acetate [obtained as is described in U.S. Pat. No. 5,302,745 or EP-A1-583 564].

LiOH (9.48 g; 0.4 mole) was dissolved in demineralized water (160 ml). A solution of methyl 3-oxo-2-pentyl-1-cyclopentene-1-acetate (10 g; 94%; 42 mmole.) in THF (200 ml) and 10 drops of ethanol were added thereto. The resulting mixture was stirred during 24 h at room temperature. Afterwards, the mixture was poured over 1000 ml of demineralized water, cooled to 0°–5° and neutralised with concentrated HCl. Extraction with dichloromethane provided 9 g of a raw oil containing about 85% of 3-oxo-2-pentyl-1-cyclopentene-1-acetic acid.

NMR(1H,360 MHz): 0.87(t, 3H); 1.2–1.4(m, 6H); 2.2(t, 2H); 2.45(m, 2H); 2.66(m, 2H); 3.5(s, 2H); 8.4(broad s, 1H)

δ ppm NMR($^{13}$C): 13.95(q); 22.44(t); 23.23(t); 27.97(t); 29.84(t); 31.79(t); 34.37(t); 36.56(t); 143.54(s); 163.86(s); 173.65(s); 210.01(s) δ ppm

EXAMPLE 3

Preparation of (−)-(1S)-cis-3-oxo-2-pentyl-1-cyclopentaneacetic acid

Prepared in identical manner to that described in Example 2, by hydrogenation of 3-oxo-2-pentyl-1-cyclopentene-1-acetic acid, in the presence of bis(trifluoroacetato)[(−)-(S)-2,2'-bis-(diphenylphosphino)-1,1'-binaphthyl] ruthenium (II) [the latter having been obtained as described in Example 2, starting from Ru(COD)(η$^3$-methallyl)$_2$ and S-BINAP (origin: Fluka)]. The (−)-(1S)-cis-3-oxo-2-pentyl-1-cyclopentaneacetic acid presented a purity analogous to that of its enantiomer described in Example 2.

EXAMPLE 4

Preparation of methyl (+)-(1R)-cis-3-oxo-2-pentyl-1-cyclopentaneacetate

A. By methylation of (+)-(1R,2S,3R)-3-hydroxy-2-pentyl-1-cyclopentaneacetic acid described in Example 1 c) and subsequent oxidation of the resulting product.

To the above-mentioned acid (2.67 g; 12.5 mmole) dissolved in 5 ml of ether, cooled by means of an ice bath, there was slowly added a solution of diazomethane in ether (0.2M), until the yellow color persisted. After addition of still a slight excess of this solution, the mixture was left at room temperature overnight. After evaporating the solvent, 2.85 g of methyl (+)-(1R,2S,3R)-3-hydroxy-2-pentyl-1-cyclopentaneacetate (purity~99%; e.r. 96.5:3.5) were obtained.

$[\alpha]_{20}^D=+17°$ (c=1.795, methanol) NMR($^1$H,360 MHz): 0.89(t, J=7, 3H); 1.22–1.50(8H); 1.53–1.93(5H); 2.32–2.52 (3H); 3.67(s, 3H); 4.20(dxt, J=4, 1.5, 1H) δ ppm NMR($^{13}$C): 14.1(q); 22.7(t); 25.1(t); 28.4(t); 29.5(t); 32.3(t); 33.7(t); 36.4(d); 36.6(t); 47.9(d); 51.4(q); 74.8(d); 174.8(s) δ ppm MS: 136(62), 84(63), 83(79), 81(71), 74(100), 67(58),55 (66), 41(62)

This ester (2.85 g) was then oxidized by means of PCC, in the presence of sodium acetate, in a manner analogous to the method described in Example 1 d), to yield 2.68 g of the desired methyl (+)-(1R)-cis-3-oxo-2-pentyl-1-cyclopentaneacetate (colorless oil; purity 98.5%; yield 92.7%).

$[\alpha]_{20}^D=+69°$ (c=1.49, methanol); +83.5° (c=1.19, chloroform) cis/trans ratio 95:5 e.r. 97.0:3.0 NMR($^1$H,360 MHz): 0.89(t,J=6.7, 3H); 1.13–1.45(7H); 1.52–1.69(1H); 1.77–1.88(m, 8 peaks, 1H); 1.95–2.08(1H); 2.08(dxd, J=15.4, 10.1, 1H); 2.14–2.33(3H); 2.39(dxd, J=15.4, 5.3, 1H); 2.83(broad septet, J=5.3), 3.70(s, 3H) δ ppm NMR ($^{13}$C): 14.0(q); 22.5(t); 24.7(t); 25.7(t); 27.2(t); 31.9(t); 33.7(t); 35.1(t); 35.8(d); 51.7(q); 52.7(d); 173.0(s); 219.2(s) δ ppm MS: 226(8,M+), 156(29), 153(29), 96(11), 83(100), 82(31), 55(23), 41(22)

By methylation of (+)-(1R)-cis-3-oxo-2-pentyl-1-cyclopentaneacetic acid described in Example 1

Upon applying to this acid the treatment with diazomethane analogous to that described under A., the desired product was obtained with similar characteristics to those described above.

C. By methylation of (+)-(1R)-cis-3-oxo-2-pentyl-1-cyclopentaneacetic acid described in Example 2

To the (+)-(1R)-cis-3-oxo-2-pentyl-1-cyclopentaneacetic acid obtained according to Example 2 (residue resulting from the concentration of the orange solution) there was added an excess of diazomethane in the form of a 2% solution in sulfuric ether and the mixture was stirred during 15 min. After concentration under reduced pressure, pentane (12 ml) was added to precipitate the catalyst. Filtering over 150 mg of silica gel (0.04–0.063 mm) in a pasteur pipette and rinsing with pentane (12 ml) were carried out. The filtrate was concentrated. Thus, 0.5 g of a mixture containing 85% of methyl (+)-(1R)-cis-3-oxo-2-pentyl-1-cyclopentaneacetate with an enantiomeric excess of 70% (determined through analysis by gas-liquid chromatography on chiral column) were obtained.

The product thus obtained was purified following the process described in Example 1, to obtain a starting (+)-(1R)-cis-3-oxo-2-pentyl-1-cyclopentaneacetic acid of enhanced purity, which was then methylated by means of diazomethane, in an analogous manner to that described above, to yield methyl (+)-(1R)-cis-3-oxo-2-pentyl-1-cyclopentaneacetate with identical purity to that of the product described under A.

EXAMPLE 5

Preparation of methyl (−)-(1S)-cis-3-oxo-2-pentyl-1-cyclopentaneacetate

This compound was prepared from (−)-(1S,2R,3S)-3-hydroxy-2-pentyl-1-cyclopentaneacetic acid [see Example 1 c)] in an analogous manner to that described in Example 4 A.

The methyl (−)-(1S)-cis-3-oxo-2-pentyl-1-cyclopentaneacetate (colorless oil; purity 98.6%) possessed identical analytical characters to those of its (+)-(1R) cis configuration enantiomer, excepting:

$[\alpha]_{20}^D=−66°$ (c=1.39, methanol); −88° (c=1.24, chloroform) cis/trans ratio 94:6 e.r. 98.0:2.0

The intermediate methyl (−)-(1S,2R,3S)-3-hydroxy-2-pentyl-1-cyclopentane acetate presented a $[\alpha]_{20}^D=−16°$ (c=1.805, methanol)

EXAMPLE 6

Preparation of methyl (+)-(1S)-trans-3-oxo-2-pentyl-1-cyclopentaneacetate and of methyl (−)-(1R)-trans-3-oxo-2-pentyl-1-cyclopentaneacetate These two optically active isomers of Hedione® were prepared by epimerization of their respective diastereomers described in Examples 4 and 5, by means of KNH$_2$ in liquid NH$_3$ at −75°.

The obtained compounds possessed analytical characters which were identical to those described in the literature [T. Kitahara et al., Agric. Biol. Chem. 50, 1867 (1986)], excepting:

(−)-(1R)-trans configuration isomer $[\alpha]_{20}^D=41°$ (c=1.15, methanol); −50° (c=1.20, chloroform) purity: 99.9% ds/trans ratio 4:96 r.e. 93.2:6.8

(+)-(1S)-trans configuration isomer $[\alpha]_{20}^D=+46°$ (c=1.08, methanol); +55° (c=1.36, chloroform) cis/trans ratio 4:96 r.e. 97.4:2.6

EXAMPLE 7

Preparation of (+)-(1R)-3-oxo-2-pentyl-1-cyclopentaneacetic acid and of methyl (+)-(1R)-3-oxo-2-pentyl-1-cyclopentaneacetate a) Preparation of lithium 3-oxo-2-pentyl-1-cyclopentene-1-acetate 3-Oxo-2-pentyl-1-cyclopentene-1-acetic acid (0.5 g; 2.38 mmole) and Li$_2$CO$_3$ (Fluka; 0.0876 g; 1.18 mmole) were mixed in water (1 ml). After 1 h stirring, there was obtained a clear solution which was concentrated to dry. The residual crystals were then dissolved in 2 ml of methanol and the obtained solution added to 20 ml of isopropyl ether for crystallization. The crystals were filtered and dried under vacuum during 60 min. The above-mentioned lithium acetate was thus obtained, in the form of very stable (decomposition at 190°) white crystals, the analytical data of which were as follows:

NMR($^1$H,360 MHz,H$_2$O): 0.87(t, 3H); 1.1–1.4(m, 6H); 2.17(t, 2H); 2.47(m, 2H); 2.68(m, 2H); 3.45(s, 2H) δ ppm
NMR($^{13}$C,H$_2$O): 16.14(q); 24.65(t); 25.07(t); 30.11(t); 33.05(t); 33.7(t); 37.19(t); 43.23(t); 143.89(s); 176.96(s); 179.76(s); 218.28(s) δ ppm MS: 193(2), 167(100), 151(54), 137(13), 123(11), 110(57), 95(10), 91(4)

The structure of the product was also confirmed by electron spray mass spectrometry.

The other analogue acetates were prepared in identical manner, by means of the appropriate carbonates, to whit, sodium, potassium, cesium, ammonium, triethylammonium carbonate and others.

The compound described above will generally be prepared in situ by admixture of the starting acid and Li$_2$CO$_3$ in water, as described above, the clear solution obtained after 1 h stirring being used as such in the hydrogenation.

b) Preparation of bis(trifluoroacetato)[(+)-(R)-BINAP-sulfonated]ruthenium (II)

We prepared the (+)-(R)-BINAP-sulfonated starting from (+)-(R)-BINAP or (+)-(R)-2,2'-bis(diphenylphosphino)-1,1'-binaphthalene (see Example 2), proceeding in identical manner to that described by Kam-to Wan et al. (ref. cited) and illustrated in the following scheme:

Scheme

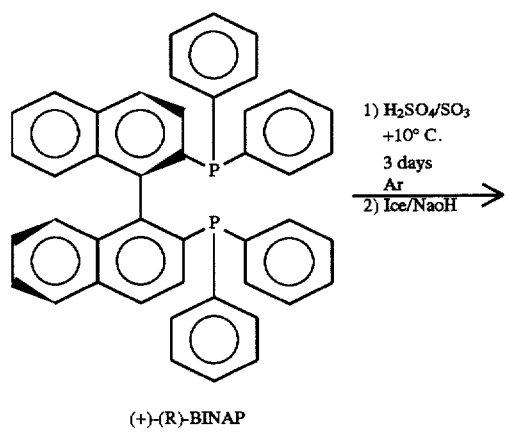

(+)-(R)-BINAP

1) H$_2$SO$_4$/SO$_3$
   +10° C.
   3 days
   Ar
2) Ice/NaOH
→

-continued
Scheme

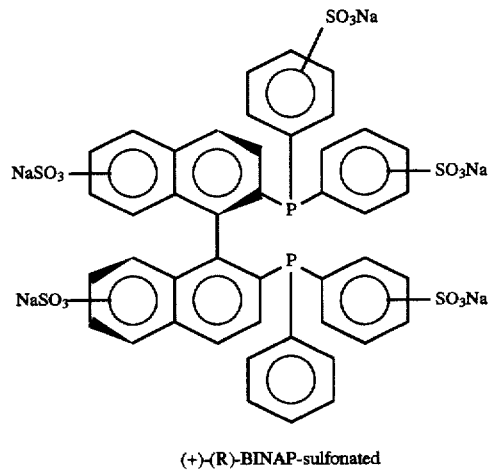

(+)-(R)-BINAP-sulfonated

The structure of the (+)-(R)-BINAP-sulfonated is represented according to the hypothesis formulated by said authors. Moreover, it is possible to increase the BINAP sulfonation, i.e. the number of SO$_3$Na groups bonded thereto, by modifying the reaction conditions.

The obtained (+)-(R)-BINAP-sulfonated (112 mg) was added to 4 ml of methanol and 2 ml of water and the solution stirred during 24 h at room temperature, under argon. This solution was then mixed with the suspension obtained by reacting Ru(COD)(η$^3$-methallyl)$_2$ and trifluoroacetic acid as is described in Example 2. The mixture was stirred during 3 days at room temperature and under Ar to obtain an almost clear brown-orange containing the desired catalyst and which was used as such in the hydrogenation.

The (−)-(S)-BINAP-sulfonated and the corresponding Ru(II) complex were prepared in an analogous manner.

c) The solutions obtained under a) and b) were mixed and the mixture stirred during 3–5 days under Ar. The resulting solution was charged in an autoclave and hydrogenated at 90×10$^5$ Pa and r.t. during 42 h until 97% conversion. The autoclave was decompressed, the reaction mixture recovered and brought to pH 3.5 by adding 1N HCl. This mixture was extracted with sulfuric ether, once with (5 ml) and once with (3 ml). The ether extract was treated with an excess of diazomethane and then concentrated. Pentane (1 ml) and a spatula of Na$_2$SO$_4$ were added to the residue and it was stirred for 5 min. It was filtered and concentrated. There were thus obtained 0.5 g of pure methyl (+)-(1R)-3-oxo-2-pentyl-1-cyclopentaneacetate (chromatography of this product indicated a cis/trans ratio of 95:5; ratio (+)-(1R)-cis/(−)-(1S)-cis 95:5, therefore 90% e.e.).

The (+) -(1R)-cis-3-oxo-2-pentyl-1-cyclopentaneacetic acid obtained in the form of the above-mentioned ether solution (before treatment with diazomethane) had the same purity characteristics as its mentioned methyl ester.

The enantiomers of these products were prepared with comparable purity in an analogous manner.

EXAMPLE 8

Preparation of (+)-(1R)-cis-3-oxo-2-pentyl-1-cyclopentaneacetic acid and of methyl (+)-(1R)-cis-3-oxo-2-pentyl-1-cyclopentaneacetate a) Preparation of bis(trifluoroacetato)[(−)-(R,R)-Et-DuPHOS]ruthenium (II)

A solution of Ru(COD)($\eta^3$-methallyl)$_2$ (48 mg; 0.15 mmole) in 3 ml of tetrahydrofuran (THF) was treated with 46 μl (0.60 mmole, 4 eq.) of CF$_3$COOH and the resulting solution stirred during 2 h at r.t. The THF and the excess of CF$_3$COOH were stripped under strong vacuum and the yellow solid thus obtained was taken in 3 ml of THF. There were added 54.3 mg (0.15 mmole) of (−)-Et-DuPHOS (origin: Strem) and the resulting solution was left under stirring at r.t. during 4 days, protected from the light. 9 Ml of methanol were then added and the obtained solution containing the desired catalyst was used as such in the following hydrogenation. All the operations were carried out under Ar and with degassed solvents.

b) To a solution of 252 mg (1.20 mmole) 3-oxo-2-pentyl-1 cyclopentene-1-acetic acid, in a mixture of 7 ml of THF and 21 ml of methanol, there were added 2 ml of the catalyst solution obtained in a) (0.025 mmole, 0.021 eq.) and 10.4 μl of triethylamine (0.075 mmole, 3 eq.) under stirring at r.t. This solution, prepared in the glass container of a standard autoclave, was introduced in this autoclave, which was locked, put under a pressure of $45 \times 10^5$ Pa of hydrogen and stirred at r.t. The reaction was followed by gas chromatography and was completed in about 4 h. After 1 night, the contents were evaporated under vacuum at r.t., the residue taken in ether, washed with HCl 10.1N and then water, dried over MgSO$_4$ and filtered. The thus obtained (+)-(1R)-3-oxo-2-pentyl-1-cyclopentaneacetic acid was esterified by means of diazomethane to yield methyl (+)-(1R)-cis-3-oxo-2-pentyl-1-cyclopentaneacetate, the chromatographic analysis (GC) of which indicated 97% purity, 96:4 cis/trans ratio and 95:5 (+)-(1R)-cis/(−)-(1S)-cis ratio.

EXAMPLE 9

Preparation of methyl (+)-cis-3-oxo-2-pentyl-1-cyclopentaneacetate a) 104 Mg (0.49 mmole) of (+)-cis-3-oxo-2-pentyl-1-cyclopentaneacetic acid (97:3 cis/trans ratio) in 0.5 ml of methanol were treated with 76 μl of dimethyl dicarbonate [CH$_3$O(CO)O(CO)OCH$_3$, origin: Bayer; 96 mg, 0.72 mmole, 1.5 eq.]. The resulting solution was heated to 45° during 16 h and then evaporated under vacuum. After distillation of the residue in a bulb-to-bulb apparatus (oven t. 150°/10 Pa), there were obtained 100 mg (0.44 mmole, yield 90%) of pure methyl (±)cis-3-oxo-2-pentyl-1-cyclopentaneacetate (97:3 cis/trans ratio).

b) To 104 mg (0.49 mmole) of (±)cis-3-oxo-2-pentyl-1-cyclopentaneacetic acid (93:7 cis/trans ratio) in 1 ml of (CH$_3$)$_2$CO there were added, first 56 μl of (CH$_3$)$_2$SO$_4$ (74 ml, 0.59 mmole, 1.2 eq.) and then 81 mg (0.59 mmole, 1.2 eq.) of anhydrous solid K$_2$CO$_3$. The resulting suspension was heated at r.t. during 4 h and taken in water and with ether. The ether phase was separated and the aqueous phase once more extracted with ether. The combined organic phases were washed with water, dried over MgSO$_4$, filtered and concentrated. The residue was distilled in a bulb-to-bulb apparatus (oven t.: 180°/7 Pa) to provide 93 mg (0.44 mmole, yield 84%) of methyl (±)-cis-3-oxo-2-pentyl-1-cyclopentaneacetate (92/8 cis/trans ratio).

When one used as starting product in the processes described above an optically active acid such as obtained in Example 8, one obtained methyl (+)-(1R)-cis-3-oxo-2-pentyl-1-cyclopentaneacetate with the same optical and stereochemical characteristics as that described in Example 8.

We claim:

1. Process for the preparation of 3-oxo-2-pentyl-1-cyclopentaneacetic acid, or of methyl 3-oxo-2-pentyl-1-cyclopentaneacetate, essentially in the form of their (+)-(1R)-cis configuration isomer, characterized in that it comprises the following steps:

a) the catalytic hydrogenation, in an appropriate solvent and in the presence of a catalyst composed of a Ru (II) complex comprising chiral ligands which contain a 2,2'-bis(diphenylphosphino)-1,1'-binaphthyl (BINAP) type ligand or a 1,2-bis(2,5-dialkylphospholano)benzenyl (DuPHOS) type ligand, wherein the alkyl is a C$_2$ or C$_3$ radical, of a compound of formula

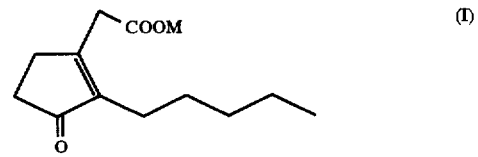

wherein M represents a hydrogen atom, an atom of an alkaline or alkaline-earth metal, or a NR$_4$ group, R representing hydrogen or a lower alkyl radical, to obtain a compound of formula

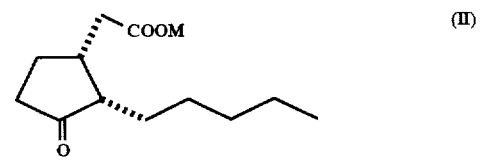

wherein M has the meaning indicated above, essentially in the form of an isomer of (+)-(1R)-cis configuration;

b) if necessary, the acidification, in a generally known manner, of the compound of formula (II) wherein M represents an atom of an alkaline or alkaline-earth metal or a NR$_4$ group, R representing hydrogen or a lower alkyl radical, to obtain (+)-(1R)-cis-3-oxo-2-pentyl-1-cyclopentaneacetic acid; and c) if necessary, the esterification, under appropriate conditions, of the (+)-(1R)-cis-3-oxo-2-pentyl-1-cyclopentaneacetic acid thus obtained to form methyl (+)-(1R)-cis-3-oxo-2-pentyl-1-cyclopentaneacetate.

2. Process according to claim 1, characterized in that 3-oxo-2-pentyl-1-cyclopentene-1-acetic acetic is subjected to catalytic hydrogenation in an organic solvent, in the presence of bis(trifluoroacetato)[(+)-(R)-BINAP]ruthenium (II) or bis(trifluoroacetato)[(−)-(R,R)-Et-DuPHOS] ruthenium (II).

3. Process according to claim 2, characterized in that the hydrogenation takes place in the presence of a nitrogen-containing organic base.

4. Process according to claim 3, characterized in that the organic base is triethylamine.

5. Process according to claim 4, characterized in that triethylamine is used in a molar ratio of 2:1 to 4:1, relative to the Ru (II) catalyst.

6. Process according to claim 2, characterized in that the organic solvent is a mixture of dichloromethane or tetrahydrofuran and methanol.

7. Process according to claim 1, characterized in that there is subjected to catalytic hydrogenation, in an appropriate solvent and in the presence of a catalyst composed of a ruthenium (II) complex and (+)-(R)-BINAP-sulfonated, a compound of formula (I) wherein M represents an atom of an alkaline or alkaline-earth metal or a $NR_4$ group, R representing hydrogen or a lower alkyl radical.

8. Process according to claim 7, characterized in that the compound of formula (I) is lithium 3-oxo-2-pentyl-1-cyclopentene-1-acetate and the catalyst is bis (trifluoroacetato)[(+)-(R)-BINAP-sulfonated]ruthenium (II).

9. Process according to claim 7, characterized in that the solvent is water or a mixture of water and methanol.

10. Process according to claim 1, characterized in that it further comprises the purification of the obtained (+)-(1R)-cis-3-oxo-2-pentyl-1-cyclopentaneacetic acid or methyl (+)-(1R)-cis-3-oxo-2-pentyl-1-cyclo-pentaneacetate, which purification comprises:

a) the reduction of methyl (+)-(1R)-cis-3-oxo-2-pentyl-1-cyclopentane-acetate by means of lithium tri-(sec-butyl)-borohydride;

b) the treatment of the thus obtained reaction mixture with $H_2O_2$ and an excess of NaOH, followed by the acidification of the resulting salt, to obtain a mixture which contains essentially (+)-(1R,2S,3R)-3-hydroxy-2-pentyl-1-cyclopentaneacetic acid and (−)-(1R,2R,3S)-3-hydroxy-2-pentyl-1-cyclopentaneacetic acid;

c) the thermal treatment of said mixture in toluene, with water separation via azeotropic distillation, followed by a treatment with potassium carbonate to isolate the formed (−)-(1R,8S)-8-pentyl-2-oxabicyclo[3.2.1] octan-3-one; and d) the treatment of this lactone with NaOH, followed by acidification, to obtain practically pure (+)-(1R,2S,3R)-3-hydroxy-2-pentyl-1-cyclopentane-acetic acid;

e) the oxidation of this acid by means of pyridinium chlorochromate, in the presence of sodium acetate; and, if necessary, f) the esterification, under appropriate conditions, of the thus formed (+)-(1R)-cis-3-oxo-2-pentyl-1-cyclopentaneacetic acid, to obtain practically pure methyl (+)-(1R)-cis-3-oxo-2-pentyl-1-cyclopentaneacetate.

11. Process according to claim 10, characterized in that the pratically pure (+)-(1R,2S,3R)-3-hydroxy-2-pentyl-1-cyclopentaneacetic acid obtained in step d) is treated, before its oxidation, with an amine of formula

(−)-(S)

wherein R represents a phenyl or 1-naphthyl radical, the resulting salt is crystallized in an appropriate organic solvent and the thus obtained crystalline salt is then acidified to obtain the above-mentioned acid with at least 95% purity.

12. Process according to claim 1, characterized in that the esterification of (+)-(1R)-cis-3-oxo-pentyl-1-cyclopentaneacetic acid is carried out by means of a. dimethyl dicarbonate in methanol; or b. a mixture of dimethyl sulfate and potassium carbonate, in an appropriate solvent.

13. Process for the preparation of (+)-(1R)-cis-3-oxo-2-pentyl-1-cyclopentaneacetic acid or of methyl (+)-(1R)-cis-3-oxo-2-pentyl-1-cyclopentaneacetate, having a purity of at least 95%, characterized in that (+)-(1R,2S,3R)-3-hydroxy-2-pentyl-1-cyclopentaneacetic acid is oxidized by means of pyridinium chlorochromate, in the presence of sodium acetate, and, if necessary, the thus formed (+)-(1R)-cis-3-oxo-2-pentyl-1-cyclopentaneacetic acid is esterified under appropriate conditions.

14. Process according to claim 13, characterized in that the starting (+)-(1R,2S,3R)-3-hydroxy-2-pentyl-1-cyclopentaneacetic acid is prepared by treating c-3-hydroxy-c-2-pentyl-r-1-cyclopentaneacetic acid with an amine of formula

(−)-(S)

wherein R represents a phenyl or 1-naphthyl radical, followed by crystallization of the thus formed salt in an appropriate organic solvent and acidification of the obtained crystalline salt.

15. Process according to claim 14, characterized in that the c-3-hydroxy-c-2-pentyl-r-1-cyclopentaneacetic acid is prepared according to a method which consists in:

a) reducing methyl 3-oxo-2-pentyl-1-cyclopentaneacetate by means of lithium tri-(sec-butyl)-borohydride;

b) treating the reaction product with $H_2O_2$ and an excess of NaOH, followed by acidification, to obtain a mixture of c-3-hydroxy-c-2-pentyl-r-1-cyclopentaneacetic and t-3-hydroxy-t-2-pentyl-r-1-cyclopentaneacetic acids;

c) thermally treating said mixture in toluene, with water separation by azeotropic distillation, followed by a treatment with potassium carbonate to isolate the formed (1RS,8SR)-8-pentyl-2-oxabicyclo [3.2.1] octan-3-one; and d) treating this lactone with NaOH, followed by acidification.

16. Process according to claim 13, characterized in that (+)-(1R)-cis-3-oxo-2-pentyl-1-cyclopentaneacetic acid is esterified by means of a. dimethyl dicarbonate in methanol; or b. a mixture of dimethyl sulfate and potassium carbonate, in an appropriate solvent.

17. Compound of formula

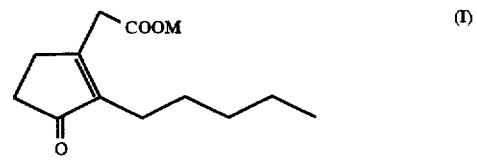

wherein symbol M represents an atom of an alkaline or alkaline-earth metal, or a $NR_4$ group, R representing hydrogen or a lower alkyl radical.

18. Compound selected from the group consisting of:

a. (+)-(1R)-cis-3-oxo-2-pentyl-1-cyclopentaneacetic acid having a stereochemical purity above 95% and an enantiomeric excess of at least 90%;

b. (+)-(1R)-cis-3-oxo-2-pentyl-1-cyclopentaneacetic acid characterized by a $[\alpha]_{20}^D$ superior to +71° (c=0.985 g/100 ml, ethanol);

c. methyl (+)-(1R)-cis-3-oxo-2-pentyl-1-cyclopentaneacetate having a stereochemical purity above 95% and an enatiomeric excess of at least 90%;

d. methyl (+)-(1R)-cis-3-oxo-2-pentyl-1-cyclopentaneacetate characterized by a $[\alpha]_{20}^D$ superior to +69° (c=1.49 g/100 ml, methanol) or above +83.5° (c=1.19 g/100 ml, chloroform);

e. (+)-(1R,2S,3R)-3-hydroxy-2-pentyl-1-cyclopentaneacetic acid, characterized by a $[\alpha]_{20}^{D}$ superior to +11° (c=1.10 g/100 ml, ethanol); and f. methyl (+)-(1R,2S,3R)-3-hydroxy-2-pentyl-1-cyclopentaneacetate, characterized by a $[\alpha]_{20}^{D}$ superior to +17° (c=1.795 g/ 100 ml, methanol).

* * * * *

UNITED STATES PATENT AND TRADEMARK OFFICE
CERTIFICATE OF CORRECTION

PATENT NO. : 5,728,866

DATED : March 17, 1998

INVENTORS : V. Rautenstrauch et al.

It is certified that error appears in the above-identified patent and that said Letters Patent is hereby corrected as shown below:

Column 18, line 1: change "(+)-(1R,25,3R)-3-hydroxy-" to --(+)-(1R,2S,3R)-3-hydroxy---.

Signed and Sealed this

Second Day of June, 1998

Attest:

BRUCE LEHMAN

Attesting Officer

Commissioner of Patents and Trademarks